United States Patent
King et al.

(10) Patent No.: US 10,597,584 B2
(45) Date of Patent: Mar. 24, 2020

(54) LEVOGLUCOSAN-BASED FLAME RETARDANT COMPOUNDS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 33 days.

(21) Appl. No.: 15/806,423

(22) Filed: Nov. 8, 2017

(65) Prior Publication Data

US 2019/0136136 A1 May 9, 2019

(51) Int. Cl.
*C09K 21/12* (2006.01)
*C09K 21/14* (2006.01)
(Continued)

(52) U.S. Cl.
CPC ............ *C09K 21/12* (2013.01); *C07F 9/6561* (2013.01); *C08F 130/02* (2013.01); *C08G 59/304* (2013.01); *C08G 59/3272* (2013.01); *C08G 64/0258* (2013.01); *C08G 65/22* (2013.01); *C08K 5/529* (2013.01); *C08K 5/5313* (2013.01);
(Continued)

(58) Field of Classification Search
CPC ......... C09K 21/12; C07H 11/04; C07H 19/01
See application file for complete search history.

(56) References Cited

U.S. PATENT DOCUMENTS 3,414,560 A * 12/1968 Carlberg ................ C07H 19/01
536/120
5,047,518 A * 9/1991 Fumeaux ............... A01N 43/90
504/196

(Continued)

FOREIGN PATENT DOCUMENTS

JP      59210987 A  * 11/1984
JP   2009084181 A  *  4/2009

OTHER PUBLICATIONS

Machine translated English language equivalent of JP 2009084181 (2009, 9 pages).*

(Continued)

*Primary Examiner* — Brieann R Johnston
(74) *Attorney, Agent, or Firm* — Kelsey M. Skodje

(57) ABSTRACT

A levoglucosan-based flame retardant compound, a process for forming a flame retardant polymer, and an article of manufacture comprising a material that contains a levoglucosan-based flame retardant polymer are disclosed. The levoglucosan-based flame retardant compound has phosphorus-based flame retardant functional groups. The process for forming the flame retardant polymer includes providing a phosphorus-based flame retardant molecule, providing levoglucosan, chemically reacting the phosphorus-based flame retardant molecule and the levoglucosan derivative to form a levoglucosan-based flame retardant compound, and incorporating the levoglucosan-based flame retardant compound into a polymer to form the levoglucosan-based flame retardant polymer.

17 Claims, 17 Drawing Sheets

(51) Int. Cl.
  *C09J 11/06* (2006.01)
  *C08K 5/5373* (2006.01)
  *C08K 5/5313* (2006.01)
  *C07F 9/6561* (2006.01)
  *C08F 130/02* (2006.01)
  *C08G 59/04* (2006.01)
  *C08G 64/02* (2006.01)
  *C08K 5/529* (2006.01)
  *C08G 59/30* (2006.01)
  *C08G 59/32* (2006.01)
  *C08G 65/22* (2006.01)

(52) U.S. Cl.
  CPC ............. *C08K 5/5373* (2013.01); *C09J 11/06* (2013.01); *C09K 21/14* (2013.01)

(56) References Cited

U.S. PATENT DOCUMENTS

| | | |
|---|---|---|
| 5,162,394 A | 11/1992 | Trocino et al. |
| 2012/0214216 A1 | 8/2012 | Brady et al. |
| 2014/0194617 A1 | 7/2014 | Boday et al. |
| 2015/0203674 A1 | 7/2015 | Weinlein et al. |
| 2015/0274848 A1 | 10/2015 | Boday et al. |
| 2016/0201257 A1* | 7/2016 | Tonani ............. C08B 5/00 8/195 |

OTHER PUBLICATIONS

Derwent Abstract of JP 59-210987 (Acc. No. 1985-015078, 1984, 2 pages).*

Hendrix (Pyrolysis and Combustion of Cellulose. II. Thermal Analysis of Mixtures of Methyl-α-D-Glucopyranoside and Levoglucosan with Model Phosphate Flame Retardants. Journal of Applied Polymer Science. 1972, 16, pp. 41-59).*

Human translation of JP 52-210987 (1984, 12 pages).*

Wodley, F., "Pyrolysis Products of Untreated and Flame Retardant-Treated α-Cellulose and Levoglucosan," Journal of Applied Polymer Science, Apr. 1971, vol. 15, pp. 835-851, John Wiley & Sons, Inc.

"Hydroxyl Groups on Levoglucosan," SciFinder results, received Feb. 23, 2017, 1 page.

* cited by examiner

100

302

352  3-Mercaptopropionate 356  2-Mercaptoethanol

360  Cysteamine HCl

600

604

$M^1, M^2, M^3 = $ 608

700

704

708

712

R = R¹ or R²

LEVOGLUCOSAN-BASED FLAME RETARDANT COMPOUNDS

BACKGROUND

The present disclosure relates to bio-renewable flame retardant compounds and, more specifically, levoglucosan-based flame retardant compounds.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Levoglucosan (6,8-dioxabicyclo[3.2.1]octane-2,3,4-triol) is one example of a bio-based compound. Levoglucosan is produced by pyrolysis of carbohydrates.

SUMMARY

Various embodiments are directed to levoglucosan-based flame retardant compounds. The levoglucosan-based flame retardant compounds have flame retardant groups, which can be phenyl-substituted flame retardant groups or functionalized flame retardant groups. The functionalized flame retardant groups can have functional groups such as allyl groups, epoxy groups, propylene carbonate groups, amino groups, carboxylic acid groups, and hydroxyl groups. Further, the flame retardant groups can include phosphonyl and/or phosphoryl moieties. The levoglucosan-based flame retardant compounds can be incorporated into a polymer to form a flame retardant polymer.

Additional embodiments are directed to a process of forming a levoglucosan-based flame retardant polymer. The levoglucosan-based flame retardant polymer can be produced by providing a phosphorus-based flame retardant molecule, providing levoglucosan, which can have one or more protecting groups, chemically reacting the phosphorus-based flame retardant molecule and the levoglucosan to form a levoglucosan-based flame retardant compound, and incorporating the levoglucosan-based flame retardant compound into a polymer to form the flame retardant polymer. The levoglucosan can come from a bio-based source. The phosphorus-based flame retardant molecule can be a phosphorus-based compound with allyl, epoxy, or phenyl groups. The levoglucosan-based flame retardant compound can have at least one functional group such as an allyl group, an epoxy group, a propylene carbonate group, a carboxylic acid group, an amine group, or a hydroxyl group. Additionally, the levoglucosan-based flame retardant compound can be incorporated into the polymer by blending, binding, or polymerizing.

Further embodiments are directed to an article of manufacture comprising a material that contains a levoglucosan-based flame retardant polymer. The article of manufacture can also contain an electronic component. Additionally, the material containing the levoglucosan-based flame retardant polymer can be a plastic for integrated circuit packing or an adhesive.

DETAILED DESCRIPTION

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can be found in fermentation technologies, membrane technologies, and genetic engineering. Biotechnological strategies can include plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame retardant properties to bio- and petroleum-based polymers. For example, flame retardant molecules or cross-linkers can be incorporated into polymers. Additionally, flame retardant monomers can be polymerized to form flame retardant polymers. Levoglucosan (6,8-dioxabicyclo[3.2.1]octane-2,3,4-triol) is one example of a bio-based compound that can have applications as a component of various polymers, resins, and monomers. Levoglucosan is obtained from the pyrolysis of carbohydrates, such as starch and cellulose.

According to the present disclosure, levoglucosan is used as a precursor for flame retardant compounds. These compounds can include small molecules, cross-linkers, monofunctional molecules, and monomers. The levoglucosan-based flame retardant compounds can be added to polymers, fabrics, resins, or other materials during blending, curing, foaming, extrusion, or other processing techniques. In addition to directly adding the levoglucosan-based flame retardant monomers to the materials during processing, the added levoglucosan-based flame retardant monomers can be contained within microcapsules.

Figure 1:
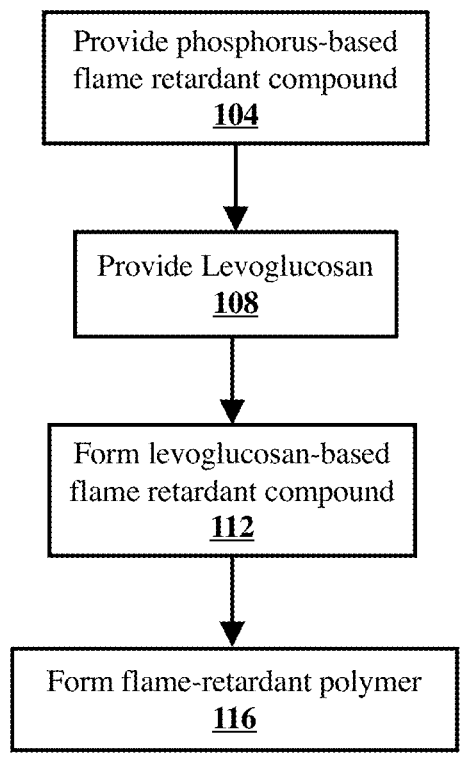
FIG. 1 is a flow diagram illustrating a process of forming a flame retardant polymer containing a levoglucosan-based flame retardant polymer.

FIG. 1 is a flow diagram illustrating a process 100 of forming a flame retardant polymer containing a levoglucosan-based flame retardant polymer. Process 100 begins with the obtainment of a phosphorus-based flame retardant molecule. This is illustrated at step 104. The phosphorus-based flame retardant molecule has either a phosphoryl or a phosphonyl moiety (collectively referred to as an FR group) with a phenyl (Ph) group and a functional group or second phenyl group. The functional groups are reactive groups involved in polymerization or binding to polymer chains. These functional groups can vary, as is discussed in greater detail below. The phosphorus-based flame retardant molecules can be phosphate- or phosphonate-based flame retardant molecules. The phosphorus-based flame retardant molecules can be synthesized as needed, or obtained from a commercial source. The structures and syntheses of phosphorus-based flame retardant molecules are discussed in greater detail with respect to FIGS. 2 and 3A-3D.

Process 100 continues with the provision of levoglucosan. This is illustrated at step 108. Levoglucosan is formed from the pyrolysis of carbohydrates, such as starch and cellulose, and can be obtained from a commercial source. Levoglucosan has a six-carbon ring structure, and includes three hydroxyl groups per ring. In some embodiments, protecting groups are attached at one or two of the three hydroxyl groups. Examples of reactions to attach these protecting groups are discussed in greater detail with respect to FIG. 4. It should be noted that the provision of levoglucosan in step 108 is illustrated as occurring after the formation of the phosphorus-based flame retardant molecule in step 104. However, in some embodiments, step 108 can occur before step 104. Further, steps 104 and 108 can occur simultaneously in some embodiments.

The protected or unprotected levoglucosan and the phosphorus-based flame retardant molecule are chemically reacted in order to form a levoglucosan-based flame retardant compound. This is illustrated at step 112. The identity of the levoglucosan-based flame retardant compound is determined by the levoglucosan (i.e., protected or unprotected) and the phosphorus-based flame retardant molecule used in the reaction. The FR groups of the phosphorus-based flame retardant compound are bonded to hydroxyl and/or carboxylic acid groups on the levoglucosan in a reaction with levoglucosan and the phosphorus-based flame retardant compounds. Additionally, in some embodiments, modifications to the FR groups (e.g., forming or attaching new functional groups) are made after binding to the levoglucosan. The syntheses and structures of levoglucosan-based flame retardant compounds are discussed in greater detail with respect to FIGS. 5A-5F.

The levoglucosan-based flame retardant compound formed in step 112 is polymerized, or added to another polymer, yielding a levoglucosan-based flame retardant polymer. This is illustrated at step 116. The levoglucosan-based flame retardant compounds can be added to a polymer as small molecules, cross-linkers, or bound monofunctional molecules. This addition can involve chemical crosslinking, mixing, blending, forming a matrix, forming a composite polymer, etc. The addition of the levoglucosan-based flame retardant compounds to the polymers can occur during blending, curing, foaming, extrusion, or other processing techniques. Further, the levoglucosan-based flame retardant compounds can be polymerized in a reaction with a base and/or a second monomer. Additionally, in some embodiments, the levoglucosan-based flame retardant compound can self-polymerize, or be polymerized in a reaction with a Ziegler-Natta catalyst. Polymerization reactions with the levoglucosan-based flame retardant compounds are discussed in greater detail with respect to FIG. 7B.

Figure 2:
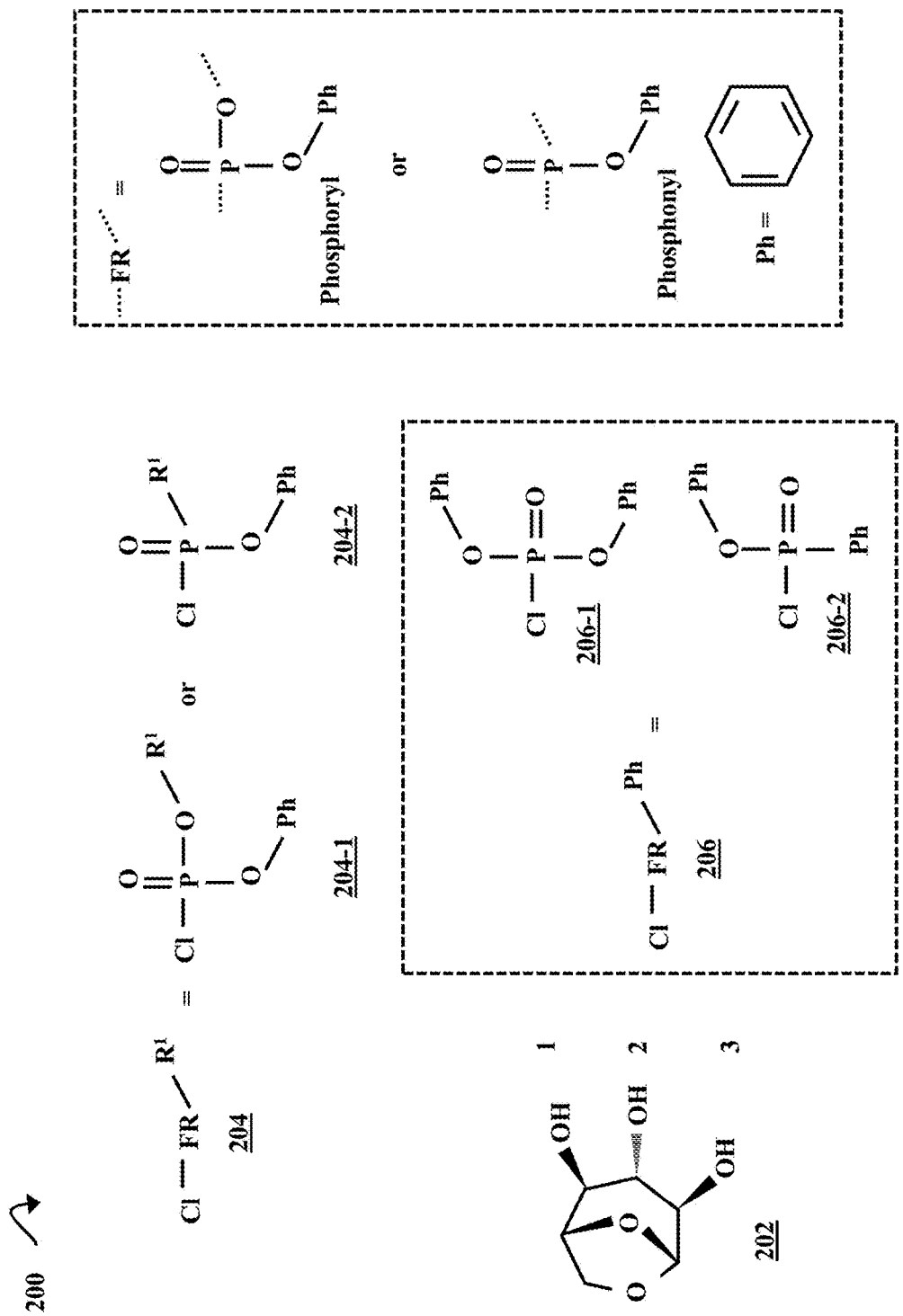
FIG. 2 is a diagrammatic representation of the molecular structures of levoglucosan, functionalized phosphorus-based flame retardant molecules, and phenyl-substituted phosphorus-based flame retardant molecules.

FIG. 2 is a diagrammatic representation of the molecular structures 200 of levoglucosan 202, functionalized phosphorus-based flame retardant molecules 204-1 and 204-2 (referred to collectively as 204) and phenyl-substituted phosphorus-based flame retardant molecules 206-1 and 206-2 (referred to collectively as 206), according to some embodiments of the present disclosure. Herein, the locations of three hydroxyl groups on levoglucosan and its derivatives are referred to from top to bottom as the first position, second position, and third position. These positions are given the numbers 1, 2, and 3, respectively, in FIG. 2.

Each phosphorus-based flame retardant molecule is either a phosphate-based flame retardant molecule 204-1 and 206-1 or phosphonate-based flame retardant molecule 204-2 and 206-2. Herein, phosphoryl and phosphonyl moieties in the phosphate- and phosphonate-based compounds, respectively, are replaced by the abbreviation "FR" in order to simplify illustrations of the molecular structures. The moieties replaced by the abbreviation each have a phenyl substituent. However, this phenyl can be replaced by another alkyl substituent (e.g., methyl, ethyl, propyl, isopropyl, etc.).

The compounds referred to as phenyl-substituted flame retardant phosphorus-based flame retardant molecules 206, each have two phenyl (Ph) substituents. The compounds referred to as $R^1$-functionalized phosphorus-based flame retardant molecules 204 each have an $R^1$ functional group in addition to a single phenyl (Ph) substituent. In some embodiments, the phenyl substituents are replaced by another alkyl substituent (e.g., methyl, ethyl, propyl, isopropyl, etc.). Example syntheses of the $R^1$-functionalized phosphorus-based flame retardant molecules 204, as well as examples of $R^1$ functional groups, are discussed with respect to FIGS. 3A and 3B. The phosphorus-based flame retardant molecules 204 and 206 are reacted with levoglucosan or levoglucosan derivatives to form levoglucosan-based flame retardant compounds. Modifications to the $R^1$ groups made in additional reactions that are carried out after the phosphorus-based compounds 204 and 206 are bound to the levoglucosan 202 result in groups referred to as $R^2$, $E^1$, and $E^2$ herein. These reactions are discussed in greater detail with respect to FIGS. 5C-5F.

Herein, levoglucosan-based flame retardant compounds are referred to as functionalized (monofunctionalized, difunctionalized, or trifunctionalized) or phenyl-substituted. Terminal functional groups attached to FR moieties (e.g., allyl, epoxy, propylene carbonate, amino, carboxylic acid, and hydroxyl groups) are involved in binding to polymer chains and/or polymerization reactions, while the phenyl substituents on the FR moieties do not participate in these reactions. Therefore, any compound with at least one functional group is referred to as functionalized to indicate that it will participate in binding or polymerization. Levoglucosan-based flame retardant compounds with only phenyl-substituents on their FR moieties are small molecules that cause a polymer to be flame retardant when blended into the polymer.

Figure 3A:
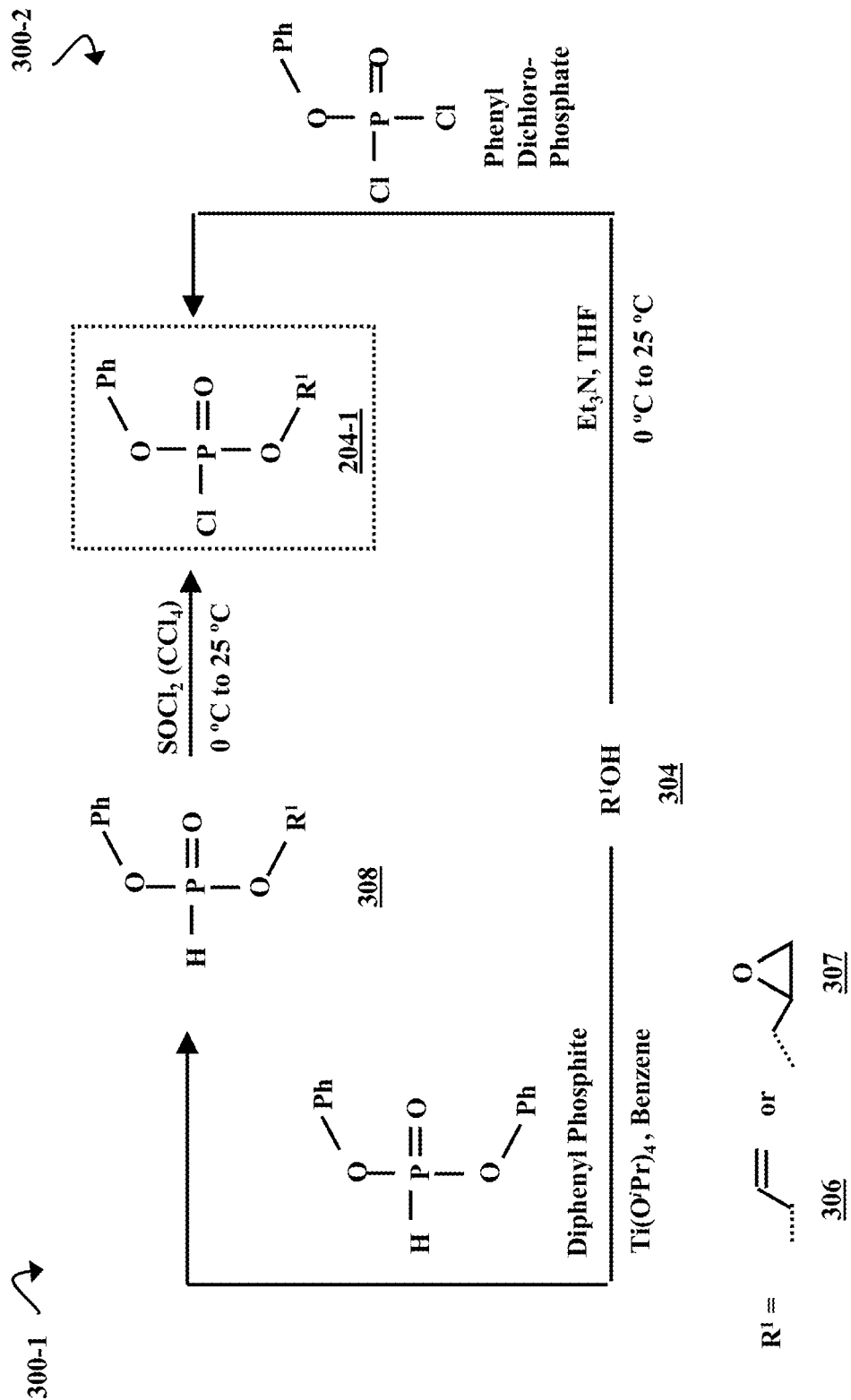
FIG. 3A is a chemical reaction diagram illustrating two processes of synthesizing an $R^1$-functionalized phosphate-based flame retardant molecule, according to some embodiments of the present disclosure.

FIG. 3A is a chemical reaction diagram illustrating two processes 300-1 and 300-2 of synthesizing an $R^1$-functionalized phosphate-based flame retardant molecule 204-1, according to some embodiments of the present disclosure. In both processes 300-1 and 300-2, an alcohol 304 is a starting material for the $R^1$-functionalized phosphate-based flame retardant molecule 204-1. The alcohol 304 has either an allyl $R^1$ group 306 or an epoxy $R^1$ group 307. It should be noted that, though $R^1$ groups with single methylene bridge groups are illustrated here, other alcohols with chains of varying lengths (e.g., one to twelve methylene bridge groups) could be used. Additionally, alcohols with acrylate substituents are used in some embodiments.

In process 300-1, the alcohol 304 is reacted with diphenyl phosphite and titanium isopropoxide (Ti(O$^i$Pr)$_4$) in benzene to produce a precursor 308 to the $R^1$-functionalized phosphate-based flame retardant molecule 204-1. In this pseudo-transesterification reaction, the precursor 308 is formed when a phenyl (Ph) substituent on diphenyl phosphite is replaced by the $R^1$ group from the alcohol 304. The precursor 308 is then reacted with thionyl chloride (SOCl$_2$) and carbon tetrachloride (CCl$_4$) over a range of approximately 0° C. to room temperature (RT, e.g., 15-25° C.), forming the $R^1$-functionalized phosphate-based flame retardant molecule 204-1. In process 300-2, the alcohol 304 is reacted with phenyl dichlorophosphate in a tetrahydrofuran (THF) solution containing triethylamine (Et$_3$N). This process is carried out over a range of approximately 0° C. to room temperature (RT, e.g., 15-25° C.). A chloride on the phenyl dichlorophosphate is replaced by the alcohol 304, forming the $R^1$-functionalized phosphate-based flame retardant molecule 204-1.

Figure 3B:
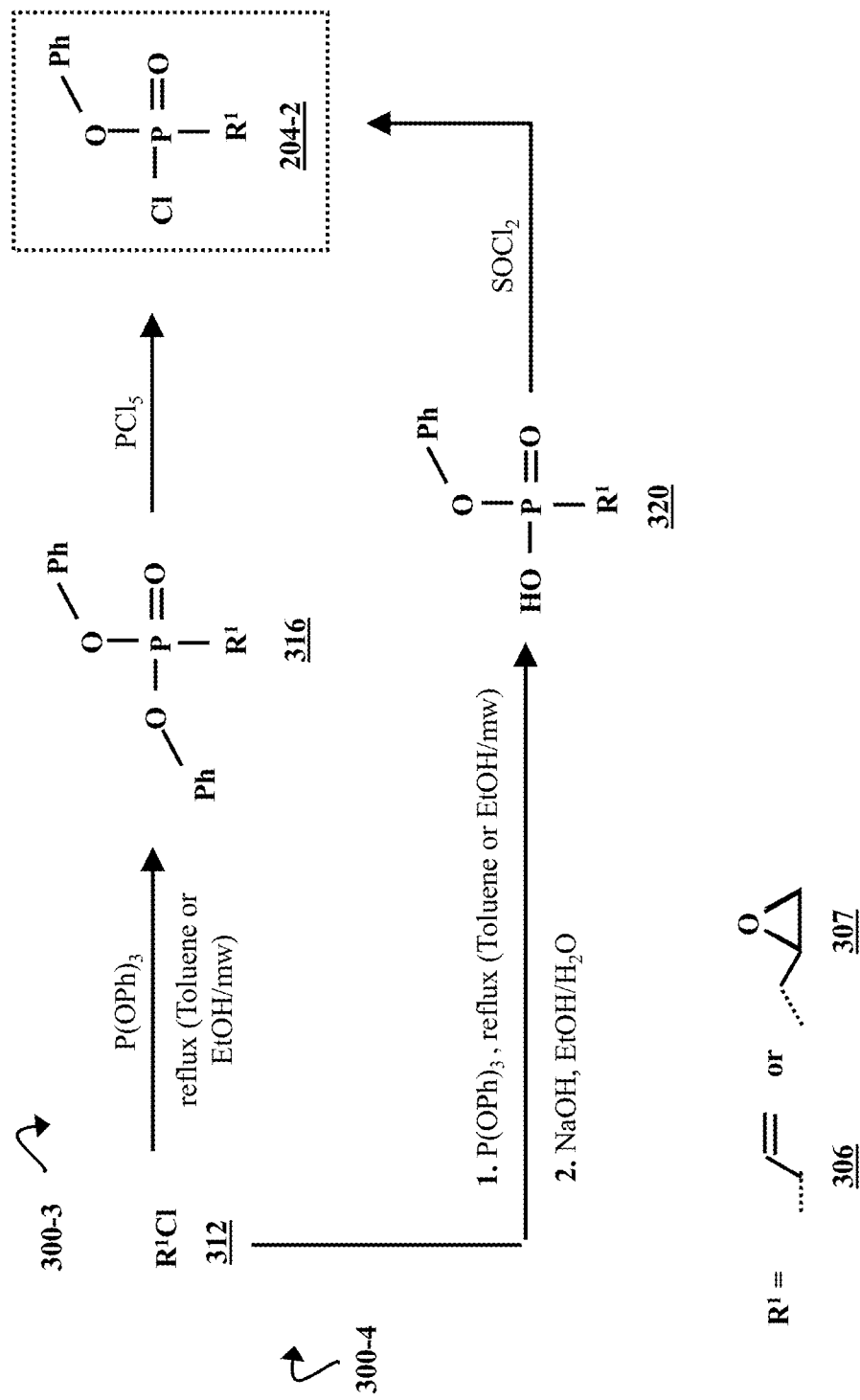
FIG. 3B is a chemical reaction diagram illustrating two processes of synthesizing an $R^1$-functionalized phosphonate-based flame retardant molecule, according to some embodiments of the present disclosure.

FIG. 3B is a chemical reaction diagram illustrating two processes 300-3 and 300-4 of synthesizing an $R^1$-functionalized phosphonate-based flame retardant molecule 204-2, according to some embodiments of the present disclosure. In both processes 300-3 and 300-4, an organochloride 312 is a starting material for the R-functionalized phosphonate-based flame retardant molecule 204-2. The organochloride has either an allyl $R^1$ group 306 or an epoxy $R^1$ group 307. It should be noted that, as in the case of the alcohol 304, organochlorides with chains of varying lengths (e.g., one to twelve methylene bridge groups) could be used. Additionally, organochlorides with acrylate substituents are used in some embodiments.

In process 300-3, the organochloride 312 is reacted with triphenyl phosphite (P(OPh)$_3$). The mixture is heated, either by refluxing in toluene or microwaving (mw) in ethanol (EtOH), producing a phosphonyl ester precursor 316 to the $R^1$-functionalized phosphonate-based flame retardant molecule 204-2. The phosphonyl ester precursor 316 is reacted with phosphorus pentachloride (PCl$_5$) to form the $R^1$-functionalized phosphonate-based flame retardant molecule 204-2.

In process 300-4, a mixture of the organochloride 312 and triphenyl phosphite (P(OPh)$_3$) is heated, either by refluxing in toluene or microwaving (mw) in ethanol (EtOH), forming a phenylphosphinic acid precursor 320 to the $R^1$-functionalized phosphonate-based flame retardant molecule 204-2. The reaction is then quenched by raising the pH of the solution. In this example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 320, producing the $R^1$-functionalized phosphonate-based flame retardant molecule 204-2.

Figure 3C:
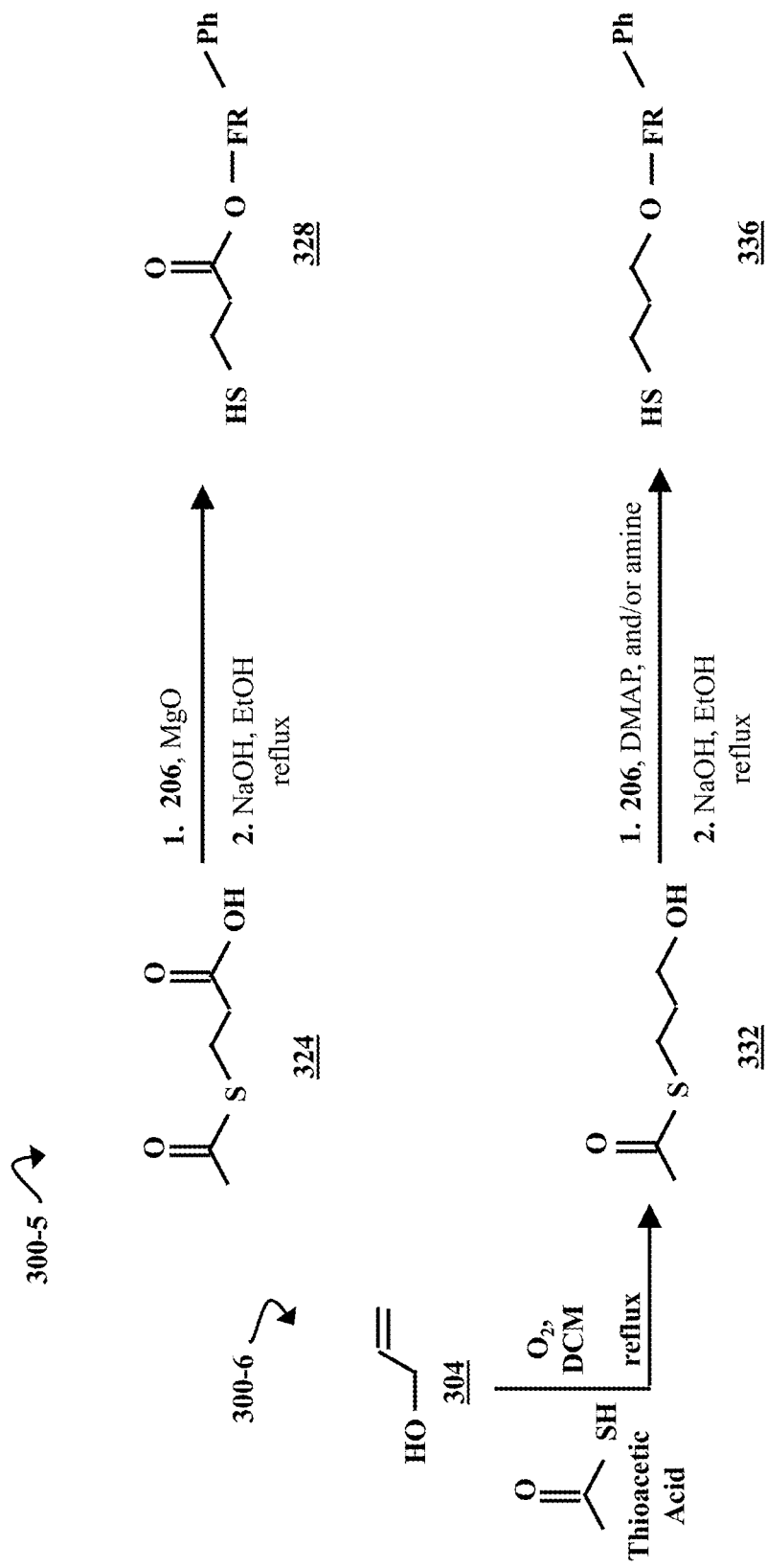
FIG. 3C is a chemical reaction diagram illustrating a process of synthesizing a carboxylic acid-derived phenyl-substituted flame retardant thiol molecule and a process of synthesizing a hydroxy-derived phenyl-substituted flame retardant thiol molecule, according to some embodiments of the present disclosure.

FIG. 3C is a chemical reaction diagram illustrating a process 300-5 of synthesizing a carboxylic acid-derived phenyl-substituted flame retardant thiol molecule 328 and a process 300-6 of synthesizing a hydroxy-derived phenyl-substituted flame retardant thiol molecule 336, according to some embodiments of the present disclosure. In process 300-5, acetate-protected thiopropionic acid 324 is reacted with magnesium oxide (MgO) and a phenyl-substituted phosphorus-based flame retardant compound 206. The acetate group is then removed by refluxing the mixture in an ethanol (EtOH) solution containing sodium hydroxide (NaOH), yielding the carboxylic acid-derived phenyl-substituted flame retardant thiol molecule 328.

In process 300-6, an alcohol 304 with an allyl R group 306 is reacted with thioacetic acid in a thiol-ene reaction. In the first step of the reaction, oxygen (O$_2$) is added to a dichloromethane (DCM) solution of the allyl alcohol 304 and thioacetic acid. The mixture is refluxed, resulting in an acetate-protected mercaptopropanol 332. The second step in the reaction is a substitution reaction involving a phenyl-substituted phosphorus-based flame retardant compound 206, catalytic dimethylaminopyridine (cat. DMAP), and/or a stoichiometric amount of an organic amine, such as triethylamine. The acetate group is removed by refluxing the mixture in an ethanol (EtOH) solution containing sodium hydroxide (NaOH). This step results in the production of the hydroxy-derived phenyl-substituted flame retardant thiol molecule 336.

Figure 3D:
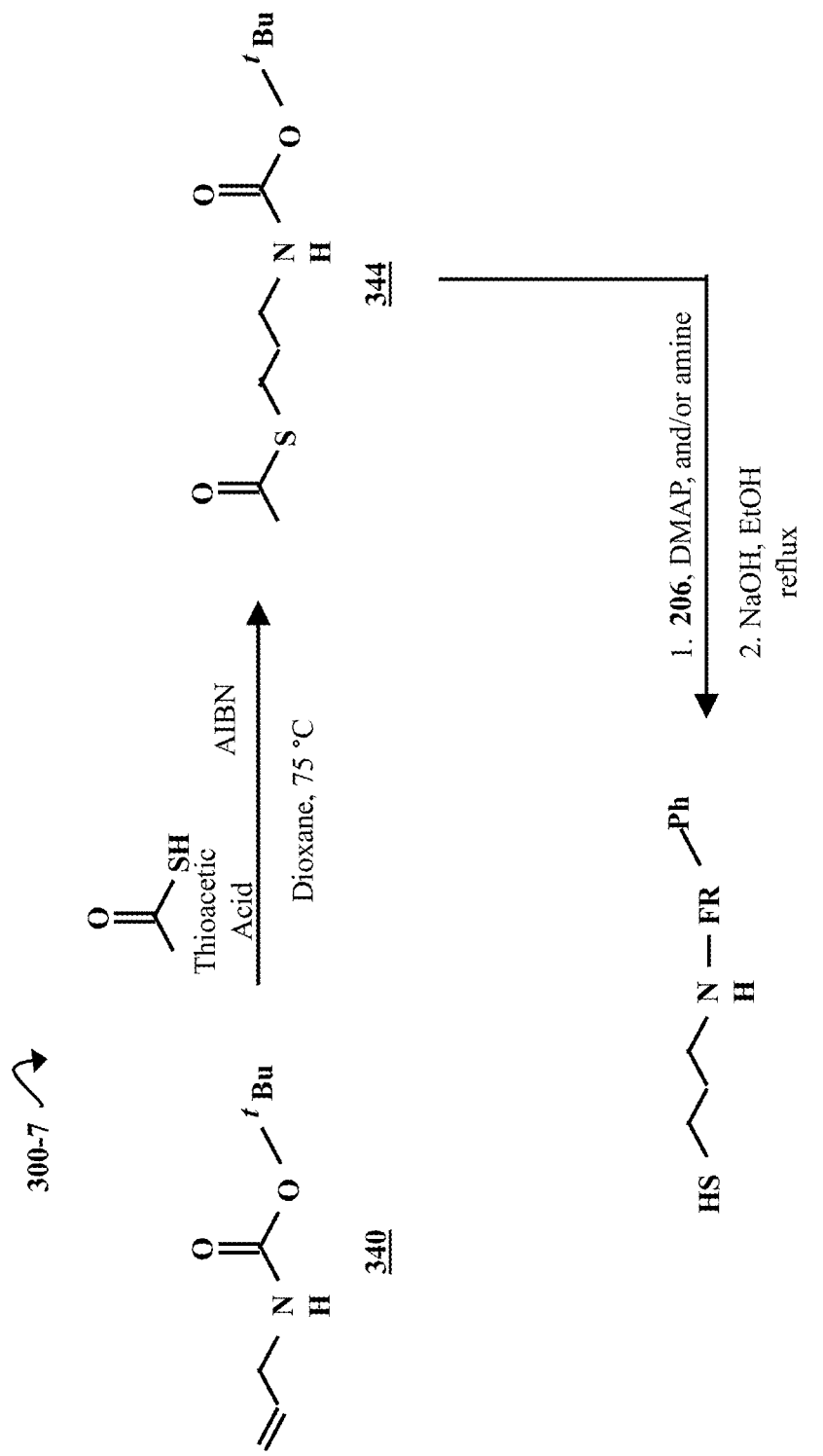
FIG. 3D is a chemical reaction diagram illustrating a process of synthesizing an amine-derived phenyl-substituted flame retardant thiol molecule, according to some embodiments of the present disclosure.

FIG. 3D is a chemical reaction diagram illustrating a process 300-7 of synthesizing an amine-derived phenyl-substituted flame retardant thiol molecule 348, according to some embodiments of the present disclosure. In process 300-7, 1-(boc-amino)-3-butene 340 is first reacted with thioacetic acid in a thiol-ene reaction. Azobisisobutyronitrile (AIBN) is added to the dioxane solution of 1-(boc-amino)-3-butene 340 and thioacetic acid, and the mixture is stirred at 75° C., resulting in an acetate-protected precursor 344 to the amine-derived phenyl-substituted flame retardant thiol molecule 348. The second step in process 300-7 is a substitution reaction with a phenyl-substituted phosphorus-based flame retardant compound 206, catalytic dimethylaminopyridine (cat. DMAP), and/or a stoichiometric amount of an organic amine, such as triethylamine. The acetate group and boc groups are removed under basic conditions (e.g., by refluxing the mixture in an ethanol (EtOH) solution containing sodium hydroxide (NaOH)). This step results in the production of the amine-derived phenyl-substituted flame retardant thiol molecule 348.

Each of the thiols produced in processes 300-5, 300-6, and 300-7 can provide phenyl-substituted thioether groups in the syntheses of $E^1$-functionalized thioether-linked levoglucosan-based flame retardant compounds. These reactions are discussed in greater detail with respect to FIG. 5E. If processes 300-5, 300-6, and 300-7 are carried out with 206-1, the resulting phenyl-substituted flame retardant thiol molecules 328, 336, and 348, respectively, will have phosphoryl FR groups, and, if the reactions are carried out with 206-2, the resulting phenyl-substituted flame retardant thiol molecules 328, 336, and 348 will have phosphonyl FR groups. Further, it should be noted that processes 300-5, 300-6, and 300-7 can be carried out with the $R^1$-functionalized phosphorus-based flame retardants 204, resulting in thiol molecules with $R^1$ functional groups. The $R^1$ functional groups attached to thiol groups that have been bound to levoglucosan can participate in any of the reactions illustrated below that involve $R^1$ functional groups and their derivatives, though these reactions are not shown.

Figure 3E:
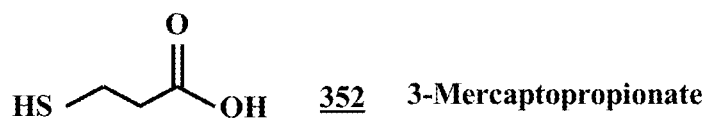
FIG. 3E is a diagrammatic representation of the molecular structures of three thiol molecules that are involved in the synthesis of the levoglucosan-based compounds, according to some embodiments of the present disclosure.
Figure 3E:
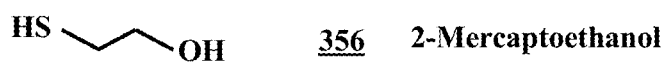
Figure 3E:
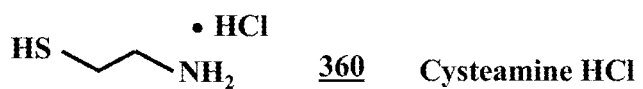

FIG. 3E is a diagrammatic representation of the molecular structures 302 of three thiol molecules that are involved in the synthesis of the levoglucosan-based compounds, according to some embodiments of the present disclosure. The three thiol molecules are 3-mercaptopropionate 352, 2-mercaptoethanol 356, and cysteamine hydrochloride (HCl) 360. Each of these thiols can provide thioethers with a functional group (e.g., carboxylic acid, hydroxyl, or amino functional groups) in the synthesis of $E^2$-functionalized thioether-linked levoglucosan-based flame retardant compounds. The syntheses and structures of the $E^2$-functionalized thioether-linked flame retardant levoglucosan-derived compounds are discussed in greater detail with respect to FIG. 5F.

Figure 4:
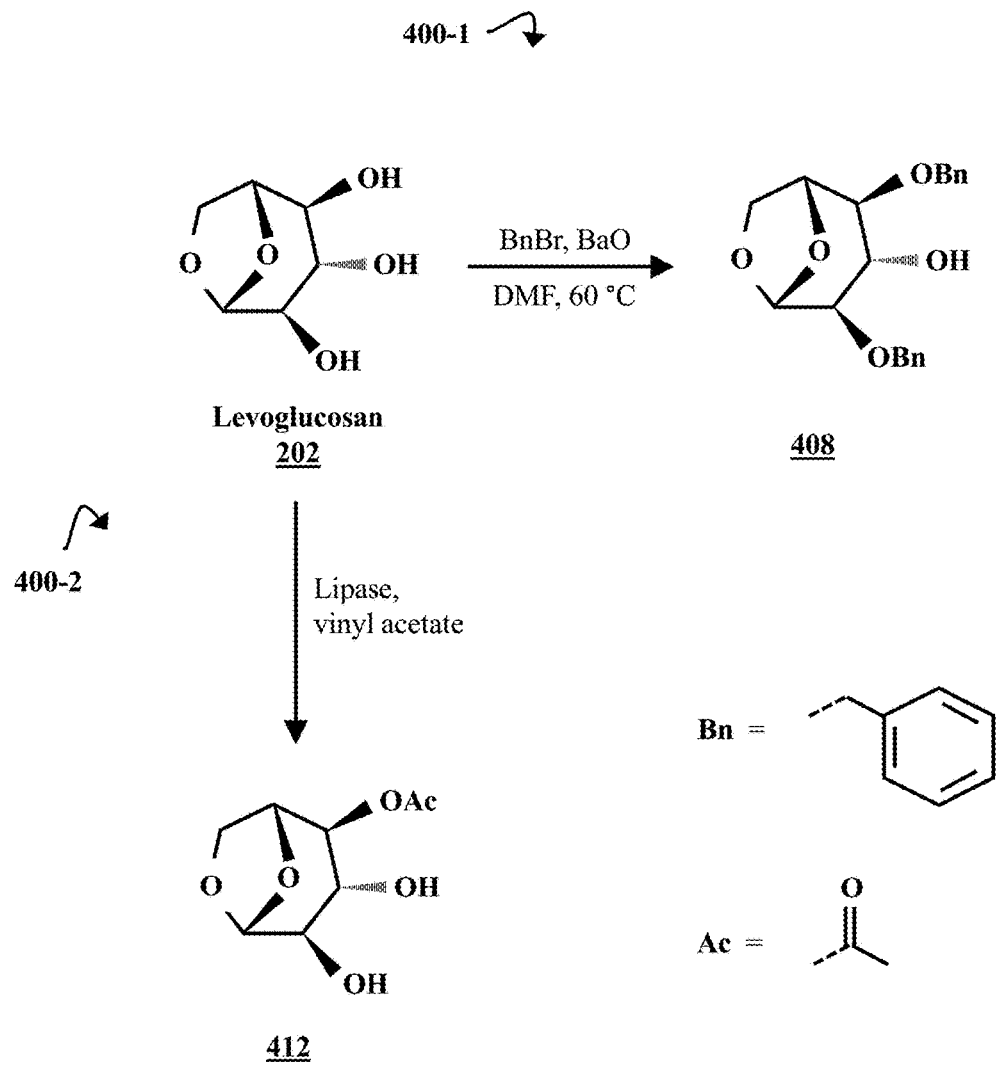
FIG. 4 is chemical reaction diagram illustrating processes of synthesizing a di-protected levoglucosan derivative and a mono-protected levoglucosan derivative, according to some embodiments of the present disclosure.

FIG. 4 is chemical reaction diagram illustrating processes 400-1 and 400-2 of synthesizing a di-protected levoglucosan derivative 408 and a mono-protected levoglucosan derivative 412, according to some embodiments of the present disclosure. In process 400-1, levoglucosan 202 is reacted at approximately 60° C. with benzyl bromide (BnBr) and barium oxide (BaO) in a dimethylformamide (DMF) solution. This reaction adds benzyl (Bn) protecting groups to the first and third positions on the levoglucosan 202, leaving one unprotected hydroxyl group at the second position. The product of this reaction is referred to as a di-protected levoglucosan 408 herein.

In process 400-2, levoglucosan 202 is reacted with vinyl acetate in a regioselective reaction catalyzed by the lipase enzyme. This reaction attaches an acetyl (Ac) protecting group at the second position on levoglucosan 202, producing a mono-protected levoglucosan 412. Subsequent reactions are carried out on levoglucosan 202 and the two protected levoglucosans 408 and 412 to form phenyl-substituted, monofunctionalized, difunctionalized, and trifunctionalized levoglucosan-based flame retardant compounds. These reactions are discussed in greater detail with respect to FIGS. 5A-5F.

Figure 5A:
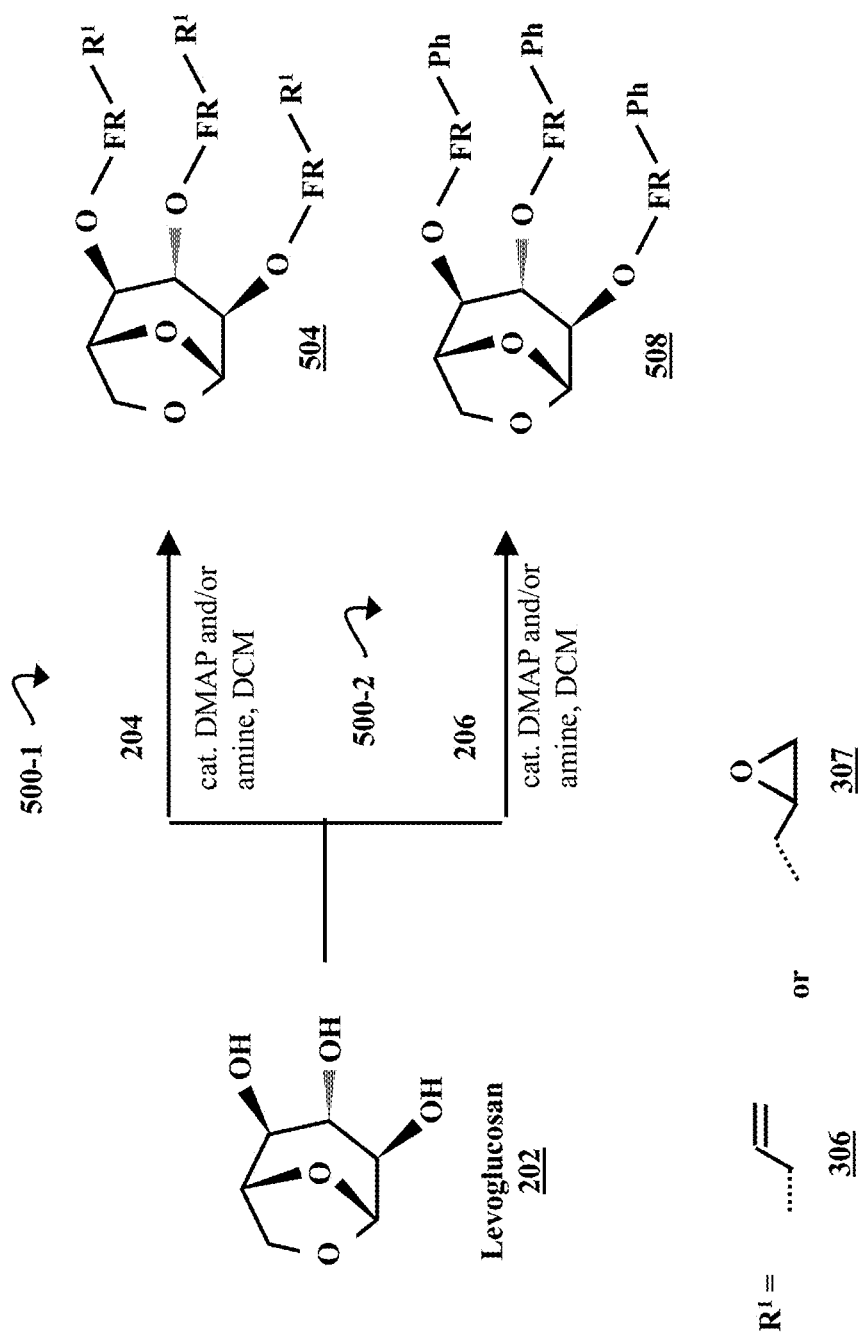
FIG. 5A is a chemical reaction diagram illustrating processes of forming an $R^1$-trifunctionalized levoglucosan-based flame retardant compound and a phenyl-substituted levoglucosan-based flame retardant compound, according to some embodiments of the present disclosure.

FIG. 5A is a chemical reaction diagram illustrating processes 500-1 and 500-2 of forming an $R^1$-trifunctionalized levoglucosan-based flame retardant compound 504 and a phenyl-substituted levoglucosan-based flame retardant compound 508, according to some embodiments of the present disclosure. In both processes 500-1 and 500-2, levoglucosan 202 is reacted with a phosphorus-based flame-retardant molecule 204 or 206, respectively, as well as catalytic dimethylaminopyridine (cat. DMAP), and/or a stoichiometric amount of an organic amine (e.g., triethylamine) in a dichloromethane (DCM) solution. The reactions attach FR moieties at the hydroxyl groups on levoglucosan 202.

In process 500-1, the reaction is carried out with an $R^1$-functionalized phosphorus-based compound 204, and allyl-306 or epoxy-307 functionalized FR moieties are attached at the hydroxyl groups on levoglucosan 202. This reaction forms an $R^1$-trifunctionalized levoglucosan-based flame retardant compound 504. This compound 504 is a levoglucosan-based flame retardant compound that can be polymerized or act as a cross-linker in another polymer. Its inclusion in a polymer, either by polymerization or cross-linking, causes the polymer to be flame retardant. Additionally, it should be noted that an epoxy $R^1$ group 307 on any of the functionalized levoglucosan-based flame retardant compounds disclosed herein can be produced by reacting an allyl functional group 306 with a peroxide reagent, such as meta-chloroperoxybenzoic acid (mCPBA). Further, epoxy $R^1$ groups 307 can ring-open in reactions involving nucleophiles.

In process 500-2, the reaction is carried out with a phenyl-substituted phosphorus-based compound 206. Phenyl-substituted FR moieties are attached at the hydroxyl groups on levoglucosan 202, and a phenyl-substituted levoglucosan-based flame retardant compound 508 is formed. This compound 508 is a levoglucosan-based flame retardant small molecule, which can be blended with a polymer to impart flame retardancy. Reactions with the phosphorus-based flame retardant compounds 204 and 206, cat. DMAP in DCM, and/or a stoichiometric amount of an organic amine can attach FR moieties to unprotected hydroxyl groups on any of the levoglucosan compounds disclosed herein (e.g., compounds 408 and 412). This is discussed in greater detail below.

Figure 5B:
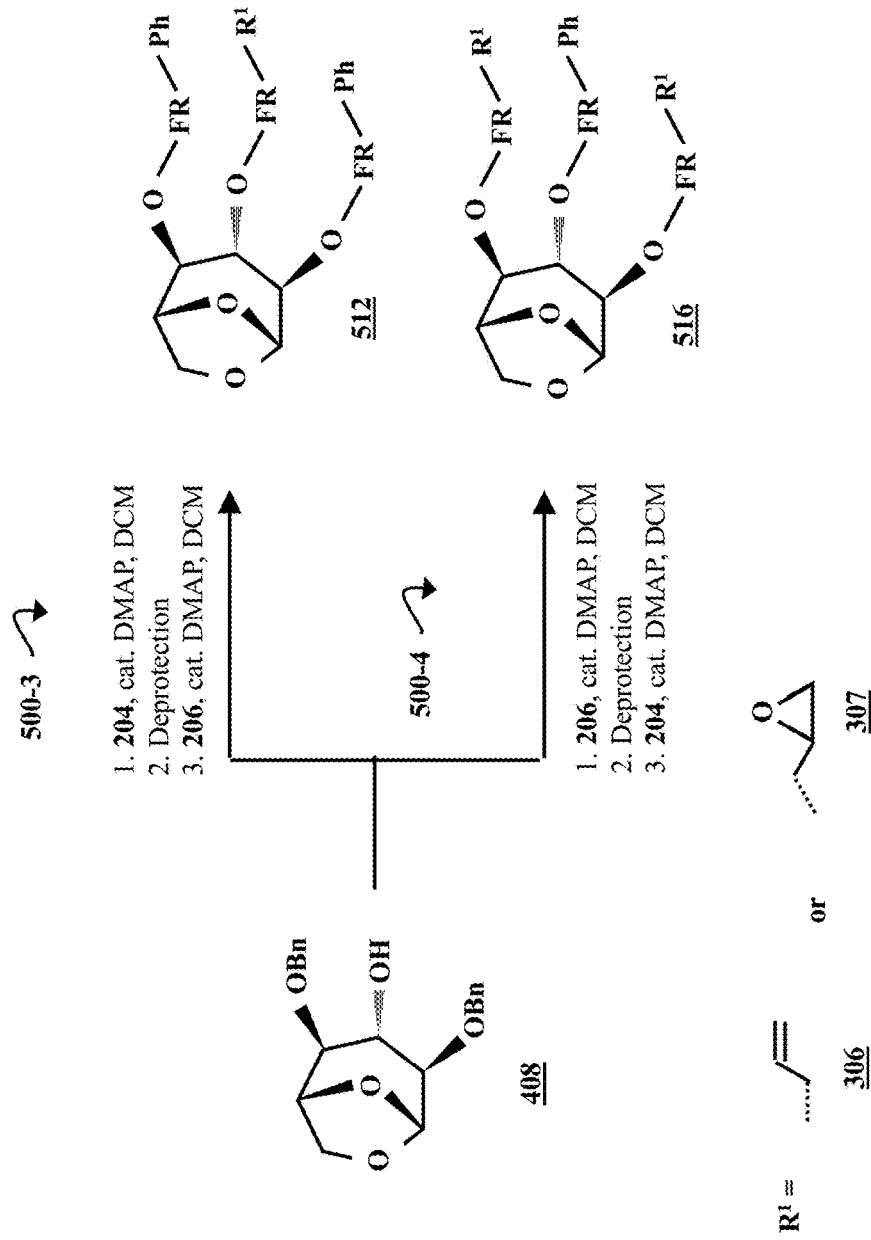
FIG. 5B is a chemical reaction diagram illustrating processes of forming an $R^1(2)$-monofunctionalized levoglucosan-based flame retardant compound and an $R^1(1,3)$-difunctionalized levoglucosan-based flame retardant compound, according to some embodiments of the present disclosure.

FIG. 5B is a chemical reaction diagram illustrating processes 500-3 and 500-4 of forming an $R^1(2)$-monofunctionalized levoglucosan-based flame retardant compound 512 and an $R^1(1,3)$-difunctionalized levoglucosan-based flame retardant compound 516, according to some embodiments of the present disclosure. The numbers in parentheses in the names of the $R^1(2)$-monofunctionalized 512 and $R^1(1,3)$-difunctionalized levoglucosan-based flame retardant compound 516 indicate the position of the $R^1$ functional group. That is, "(2)" indicates that an $R^1$ functional group is at the second position, and "(1,3)" indicates that $R^1$ functional groups are at the first and third positions. Parenthetical numbers are used in this way in naming each of the mono- or difunctionalized levoglucosan-based flame-retardant compounds disclosed herein.

In the first step of both processes 500-3 and 500-4, the di-protected levoglucosan 408 is reacted with a phosphorus-based flame-retardant molecule 204 or 206, respectively. The selected phosphorus-based flame-retardant molecule 204 or 206 is reacted with the di-protected levoglucosan 408, catalytic dimethylaminopyridine (cat. DMAP) and/or a stoichiometric amount of an organic amine (e.g., triethylamine) in a dichloromethane (DCM) solution. These reaction conditions cause the phosphorus-based flame retardant molecule 204 or 206 to attach FR moieties at the unprotected hydroxyl group on the di-protected levoglucosan 408. The intermediate products of the first and second steps in processes 500-3 and 500-4 are not shown.

In the second step in both processes 500-3 and 500-4, the Bn protecting groups are removed in a deprotection reaction. In the deprotection reaction, the Bn-protected products of the first steps are deprotected by hydrogenolysis (e.g., a reaction with hydrogen ($H_2$) catalyzed by palladium (Pd) in an ethanol solution). Removal of the benzyl (Bn) group can also be accomplished by reaction with an oxidizing agent (e.g., chromium trioxide ($CrO_3$)/acetic acid, ozone, N-bromosuccinimide, N-iodosuccinimide, etc.) or a reducing agent such as $Na/NH_3$ or $Li/NH_3$. Additionally, this deprotection can be carried out via a Lewis acid reaction with trimethylsilyl iodide in dichloromethane.

In the third step in process 500-3, the deprotected compound is reacted with a phenyl-substituted phosphorus-based flame retardant compound 206, cat. DMAP and/or a stoichiometric amount of an organic amine (e.g., triethylamine) in a DCM solution. This reaction produces the $R^1$(2)-monofunctionalized levoglucosan-based flame retardant compound 512. In the third step in process 500-4, the deprotected compound is reacted with an $R^1$-substituted phosphorus-based flame retardant compound 204, cat. DMAP and/or a stoichiometric amount of an organic amine (e.g., triethylamine) in a DCM solution. This reaction produces the $R^1$(1,3)-difunctionalized levoglucosan-based flame retardant compound 516. The functionalized levoglucosan compounds 512 and 516 can be polymerized to form a flame retardant polymer. Additionally, the $R^1$(1,3)-difunctionalized levoglucosan-based flame retardant compound 516 can be added to a polymer as a cross-linker, and the $R^1$(2)-monofunctionalized levoglucosan-based flame retardant compound 512 can be bound to polymer chains. Their inclusion in a polymer, either by polymerization, cross-linking, or binding to single locations on the polymer chain, causes the polymer to be flame retardant.

Figure 5C:
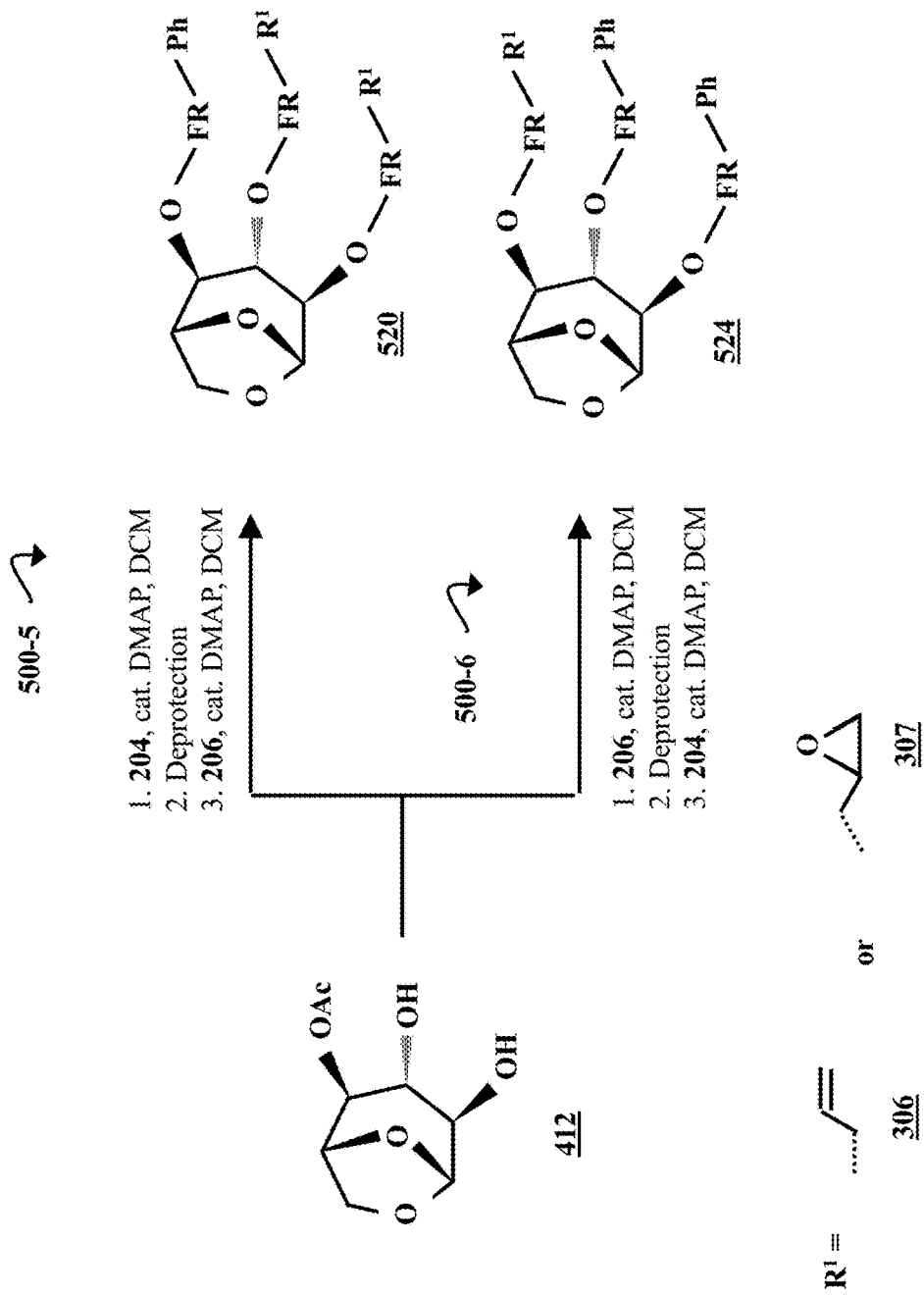
FIG. 5C is a chemical reaction diagram illustrating processes of forming an $R^1(2,3)$-difunctionalized levoglucosan-based flame retardant compound and an $R^1(1)$-monofunctionalized levoglucosan-based flame retardant compound, according to some embodiments of the present disclosure.

FIG. 5C is a chemical reaction diagram illustrating processes 500-5 and 500-6 of forming an $R^1$(2,3)-difunctionalized levoglucosan-based flame retardant compound 520 and an $R^1$(1)-monofunctionalized levoglucosan-based flame retardant compound 524, according to some embodiments of the present disclosure. In the first step of both processes 500-5 and 500-6, the mono-protected levoglucosan 412 is reacted with a phosphorus-based flame-retardant molecule 204 or 206, respectively. The selected phosphorus-based flame-retardant molecule 204 or 206 is reacted with the mono-protected levoglucosan 412, catalytic dimethylaminopyridine (cat. DMAP) and/or a stoichiometric amount of an organic amine (e.g., triethylamine) in a dichloromethane (DCM) solution. These reaction conditions cause the phosphorus-based flame retardant molecule 204 or 206 to attach FR moieties to the unprotected hydroxyl groups at the second and third positions on the mono-protected levoglucosan 412. The intermediate products of the first and second steps in processes 500-5 and 500-6 are not shown.

In the second step in both processes 500-5 and 500-6, the acetyl (Ac) protecting group is removed in a deprotection reaction. In the deprotection reaction, the Ac-protected products of the first steps are reacted with an acid in an ethanol solution. However, other deprotection conditions can include an aqueous acid at approximately pH 2 or lower, an aqueous base at approximately pH 9 or higher, or an anhydrous base in methanol. In the third step in process 500-3, the deprotected compound is reacted with a phenyl-substituted phosphorus-based flame retardant compound 206, cat. DMAP and/or a stoichiometric amount of an organic amine (e.g., triethylamine) in a DCM solution. This reaction produces the $R^1$(2,3)-difunctionalized levoglucosan-based flame retardant compound 520.

In the third step in process 500-4, the deprotected product of the first step is reacted with an $R^1$-substituted phosphorus-based flame retardant compound 204, cat. DMAP and/or a stoichiometric amount of an organic amine (e.g., triethylamine) in a DCM solution. This reaction produces the $R^1$(1)-monofunctionalized levoglucosan-based flame retardant compound 524. The functionalized levoglucosan compounds 520 and 524 can be polymerized to form a flame retardant polymer. Additionally, the $R^1$(2,3)-difunctionalized levoglucosan-based flame retardant compound 520 can be added to a polymer as a cross-linker, and the $R^1$(1)-monofunctionalized levoglucosan-based flame retardant compound 524 can be bound to polymer chains. Their inclusion in a polymer, either by polymerization, cross-linking, or binding to single locations on the polymer chain, causes the polymer to be flame retardant.

Figure 5D:
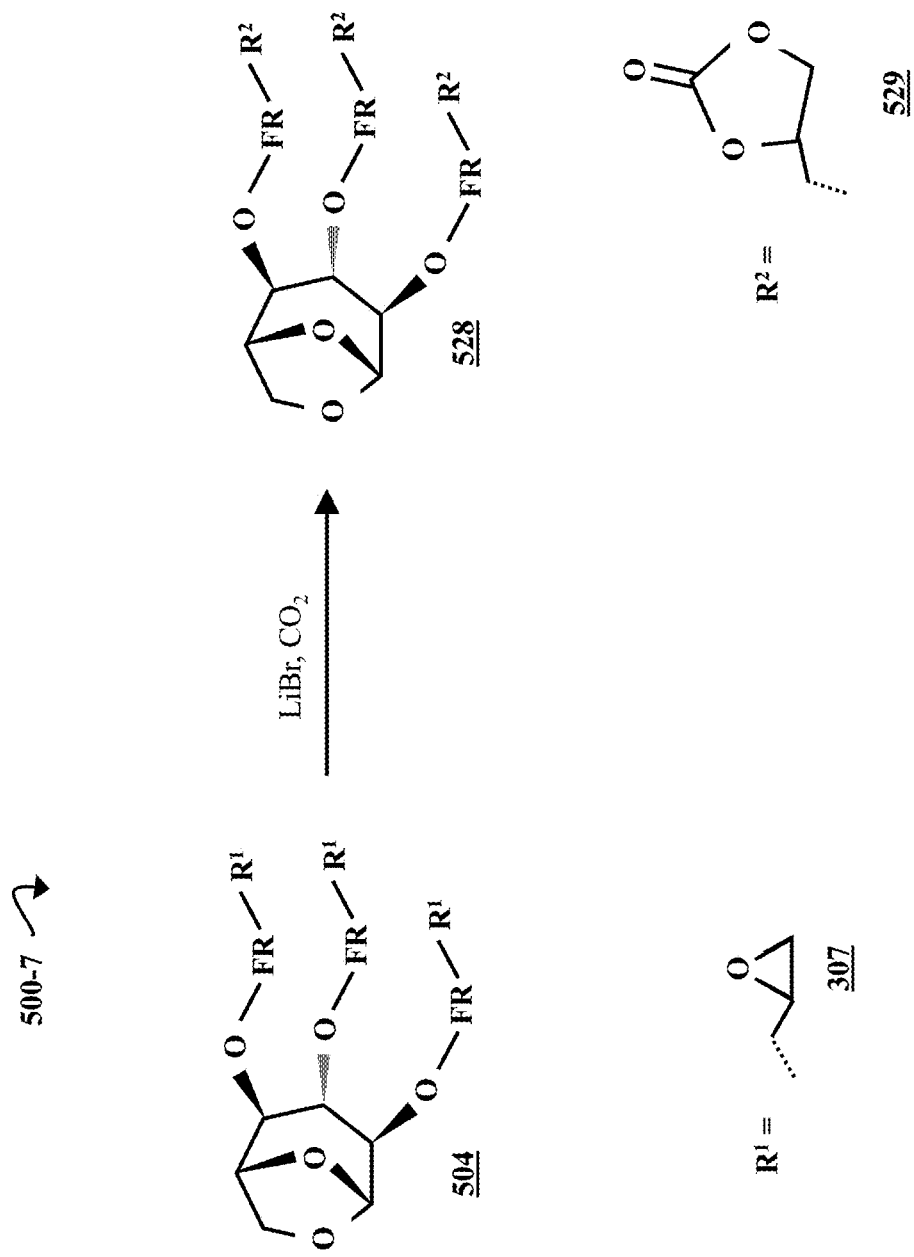
FIG. 5D is a chemical reaction diagram illustrating a process of forming an $R^2$-trifunctionalized levoglucosan-based flame retardant compound, according to some embodiments of the present disclosure.

FIG. 5D is a chemical reaction diagram illustrating a process 500-7 of forming an $R^2$-trifunctionalized levoglucosan-based flame retardant compound 528, according to some embodiments of the present disclosure. In this reaction the $R^1$-trifunctionalized levoglucosan-based flame retardant compound 504 having an epoxy $R^1$ group 307 is combined with lithium bromide (LiBr) in an appropriate solvent (e.g., methanol, ethanol, ether, acetone, etc.). Carbon dioxide ($CO_2$) is added to the mixture, either by bubbling or by injecting into the headspace of a flask containing the mixture. The $CO_2$ reacts with the epoxy $R^1$ groups 307 to form propylene carbonate $R^2$ groups 529, thereby producing an $R^2$-trifunctionalized levoglucosan-based flame retardant compound 528.

Analogous $LiBr/CO_2$ reactions can be carried out with any of the epoxy-functionalized levoglucosan-based flame retardant compounds disclosed herein to form propylene carbonate ($R^2$ 529) mono- or difunctionalized levoglucosan-based flame retardant compounds. For example, $LiBr/CO_2$ reactions with the $R^1$(2)-monofunctionalized levoglucosan-based flame retardant compound 512 and the $R^1$(1,3)-difunctionalized levoglucosan-based flame retardant compound 516 produce an $R^2$(2)-monofunctionalized levoglucosan-based flame retardant compound and an $R^2$(1,3)-difunctionalized levoglucosan-based flame retardant compound, respectively. Further, $LiBr/CO_2$ reactions with the $R^1$(2,3)-difunctionalized levoglucosan-based flame retardant compound 520 and the $R^1$(1)-monofunctionalized levoglucosan-based flame retardant compound 524 produce an $R^2$(2,3)-difunctionalized levoglucosan-based flame retardant compound and an $R^2$(1)-monofunctionalized levoglucosan-based flame retardant compound, respectively. These $R^2$-mono- and difunctionalized compounds are not illustrated herein.

The $R^2$-mono-, di-, and trifunctionalized levoglucosan-based flame retardant compounds can be polymerized to form a flame retardant polymer. Additionally, the $R^2$-di- and trifunctionalized levoglucosan-based flame retardant compounds can be added to a polymer as a cross-linker, and the $R^2$-monofunctionalized levoglucosan-based flame retardant compounds can be bound to polymer chains. The inclusion of these $R^2$-functionalized levoglucosan-based flame retardant compounds in a polymer, either by polymerization, cross-linking, or binding to single locations on the polymer chain, causes the polymer to be flame retardant.

Figure 5E:
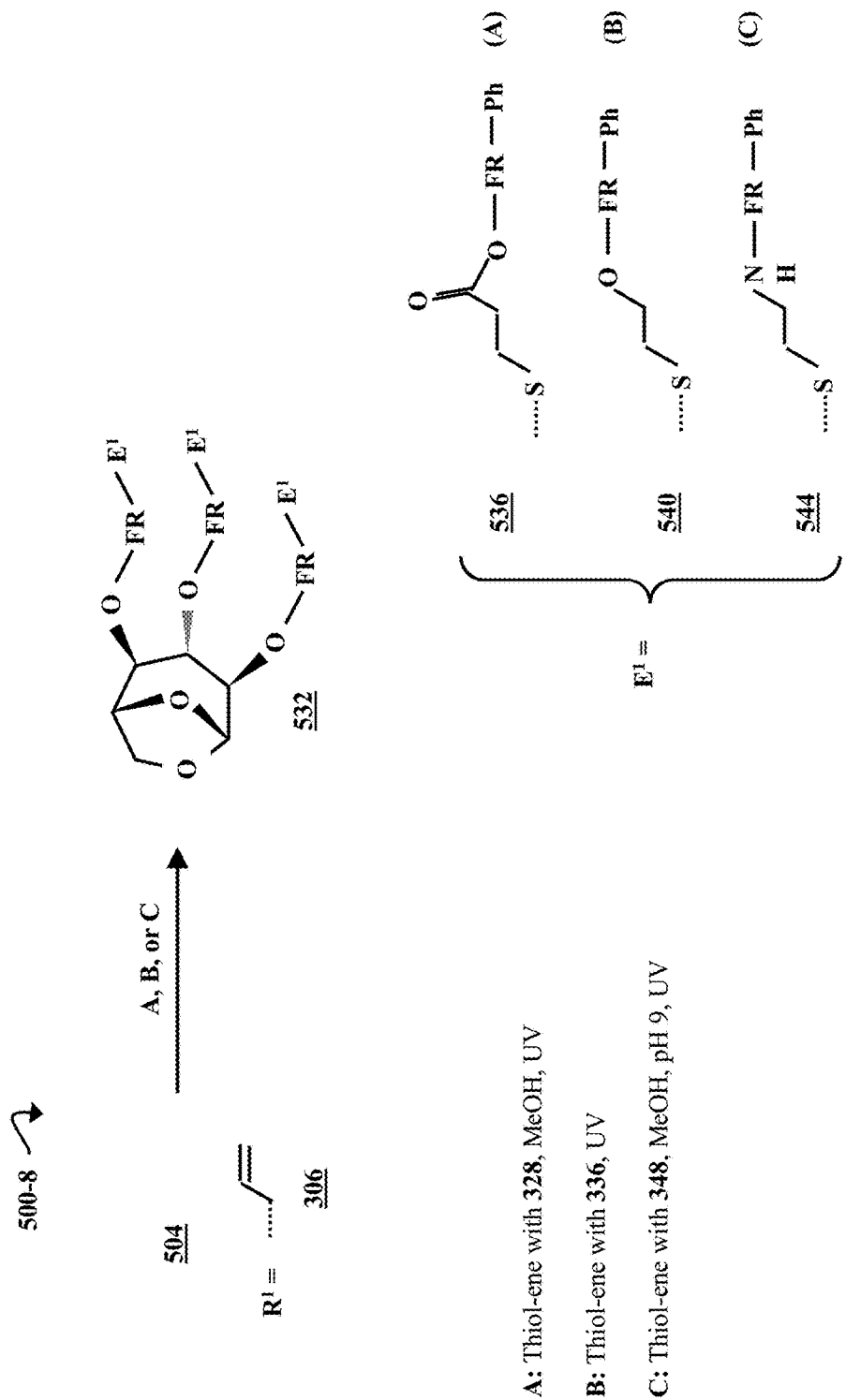
FIG. 5E is a chemical reaction diagram illustrating a process of forming phenyl-substituted $E^1$ thioether-linked levoglucosan-based flame retardant compounds, according to some embodiments of the present disclosure.

FIG. 5E is a chemical reaction diagram illustrating a process 500-8 of forming phenyl-substituted $E^1$ thioether-linked levoglucosan-based flame retardant compounds 532, according to some embodiments of the present disclosure. The phenyl-substituted thioether groups are referred to as $E^1$ groups 536, 540, or 544 herein, and are bound to FR moieties on the levoglucosan-based flame retardant compounds 532. Process 500-8 can be carried out under reaction conditions A, B, or C. Each of these reaction conditions is a thiol-ene reaction between the $R^1$-trifunctionalized levoglucosan-based flame retardant compound 504 with allyl $R^1$ groups 306 and a phenyl-substituted flame retardant thiol molecule 328, 336, or 348. The syntheses and structures of the phenyl-substituted flame retardant thiol molecules are discussed in greater detail with regard to FIGS. 3C and 3D.

The thiol molecules react with allyl $R^1$ groups 306 on the $R^1$-trifunctionalized levoglucosan-based flame-retardant compound 504. The phenyl-substituted $E^1$ thioether-linked flame-retardant levoglucosan-based compounds 532 are flame retardant small molecules that can be blended with polymers to impart flame retardancy. It should be noted that the reactions can also be carried out with the mono- and di-functionalized levoglucosan-based flame retardant compounds 512, 516, 520, and 524 having allyl $R^1$ groups 306, resulting in analogous mono- and di-$E^1$ thioether-linked levoglucosan-based flame retardant compounds.

Under thiol-ene reaction conditions A, the $R^1$-trifunctionalized levoglucosan-based flame-retardant compound 504 having allyl $R^1$ groups 306 is reacted with the phenyl-substituted carboxylic acid-derived phenyl-substituted flame-retardant thiol molecule 328 under UV light in a methanol (MeOH) solution. The resulting phenyl-substituted $E^1$ thioether-linked levoglucosan-based flame retardant compound 532 has thioether $E^1$ groups 536 that correspond to the carboxylic acid-derived phenyl-substituted flame-retardant thiol molecule 328.

Under thiol-ene reaction conditions B, the $R^1$-trifunctionalized levoglucosan-based flame-retardant compound 504 having allyl $R^1$ groups 306 is reacted with the phenyl-substituted hydroxy-derived phenyl-substituted flame retardant thiol molecule 336 under UV light. The resulting phenyl-substituted $E^1$ thioether-linked levoglucosan-based flame retardant compound 532 has thioether $E^1$ groups 540 that correspond to the hydroxy-derived phenyl-substituted flame retardant thiol molecule 336.

Under thiol-ene reaction conditions C, the $R^1$-trifunctionalized levoglucosan-based flame-retardant compound 504 having allyl $R^1$ groups 306 is reacted with the phenyl-substituted amine-derived phenyl-substituted flame retardant thiol molecule 348 under UV light in a pH 9 methanol solution. The resulting phenyl-substituted $E^1$ thioether-linked levoglucosan-based flame retardant compound 532 has thioether $E^1$ groups 544 that correspond to the amine-derived phenyl-substituted flame retardant thiol molecule 348.

Figure 5F:
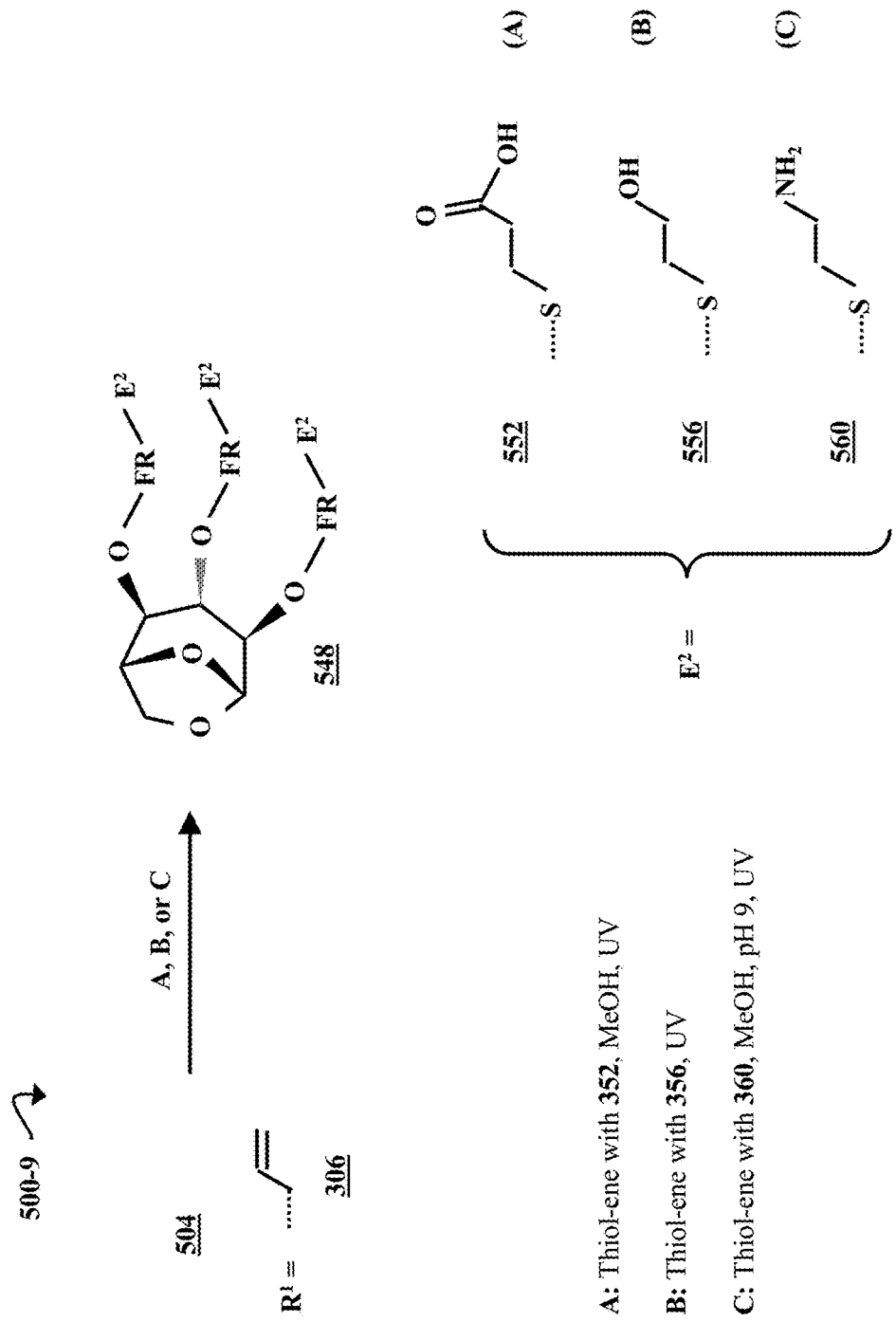
FIG. 5F is a chemical reaction diagram illustrating a process of forming trifunctionalized $E^2$ thioether-linked levoglucosan-based flame retardant compounds, according to some embodiments of the present disclosure.

FIG. 5F is a chemical reaction diagram illustrating a process 500-9 of forming trifunctionalized $E^2$ thioether-linked levoglucosan-based flame retardant compounds 548, according to some embodiments of the present disclosure. The functionalized thioether groups are referred to as $E^2$ groups 552, 556, and 560 herein, and are bound to FR moieties on the levoglucosan-based flame retardant compounds 548. Process 500-9 can be carried out under reaction conditions A, B, or C. Each of these reaction conditions is a thiol-ene reaction between the $R^1$-trifunctionalized levoglucosan-based flame retardant compound 504 having allyl $R^1$ groups 306 and a thiol molecule (3-mercaptopropionate 352, 2-mercaptoethanol 356, or cysteamine hydrochloride (HCl) 360).

Each thiol molecule reacts with an allyl $R^1$ group 306 on the $R^1$-trifunctionalized levoglucosan-based flame-retardant compound 504, forming $E^2$-trifunctionalized levoglucosan-based compounds 548. It should be noted that the reactions can also be carried out with the mono- and di-functionalized levoglucosan-based flame retardant compounds 512, 516, 520, and 524 having allyl $R^1$ groups 306. Carrying out process 500-9 with an $R^1$-monofunctionalized 512 or 524 or $R^1$-difunctionalized 516 or 520 levoglucosan-based flame retardant compound forms an $E^2$-monofunctionalized or an $E^2$-difunctionalized thioether-linked levoglucosan-based flame retardant compound, respectively. The $E^2$-tri-548, $E^2$-di-, and $E^2$-monofunctionalized thioether-linked levoglucosan-based flame retardant compounds can bind to polymers, and/or act as cross-linkers, causing the polymers to be flame retardant.

Under thiol-ene reaction conditions A, the $R^1$-trifunctionalized levoglucosan-based flame retardant compound 504 having allyl $R^1$ groups 306 is reacted with 3-mercaptopropionate 352 under UV light in a methanol (MeOH) solution. The resulting $E^2$-trifunctionalized thioether-linked levoglucosan-based flame retardant compound 548 has carboxylic acid-functionalized thioether $E^2$ groups 552 that correspond to the 3-mercaptopropionate 352. Under thiol-ene reaction conditions B, the $R^1$-trifunctionalized levoglucosan-based flame retardant compound 504 having allyl $R^1$ groups 306 is reacted with 2-mercaptoethanol 356 under UV light. The resulting $E^2$-trifunctionalized thioether-linked flame-retardant levoglucosan-based compound 548 has hydroxyl-functionalized thioether $E^2$ groups 556 that correspond to the 2-mercaptoethanol 356. Under thiol-ene reaction conditions C, the $R^1$-trifunctionalized levoglucosan-based flame retardant compound 504 having allyl $R^1$ groups 306 is reacted with cysteamine HCl 360 under UV light in a pH 9 methanol solution. The resulting $E^2$-trifunctionalized thioether-linked flame-retardant levoglucosan-based compound 548 has amine-functionalized thioether groups 560 that correspond to the cysteamine HCl 360.

The processes of forming the levoglucosan-based flame retardant compounds illustrated herein can be carried out with different combinations of phosphorus-based flame retardant molecules 204 and 206. In some embodiments, these processes can be carried out with either all phosphate-based flame retardant molecules (204-1 and/or 206-1) or all phosphonate-based flame retardant molecules (204-2 and/or 206-2). In other embodiments, a mixture of both phosphate-phosphonate-based flame retardant molecules can be used. Carrying out these processes with a mixture of phosphate- and phosphonate-based compounds (206-1/206-2 and/or 204-1/204-2) can result in the production of levoglucosan-based flame retardant monomers with both phosphoryl and phosphonyl FR groups.

However, in some instances, adding a mixture of phosphate- and phosphonate-based compounds (206-1/206-2 or 204-1/204-2) can result in the production of levoglucosan-based flame retardant monomers with all phosphoryl or all phosphonyl FR moieties. Additionally, adding a mixture of phosphate- and phosphonate-based compounds (206-1/206-2 or 204-1/204-2) to the reaction can yield a mixture of products that includes some combination of levoglucosan-based flame retardant monomers with either all phosphoryl or all phosphonyl FR groups and levoglucosan-based flame retardant monomers with both phosphoryl and phosphonyl FR groups.

Figure 6:
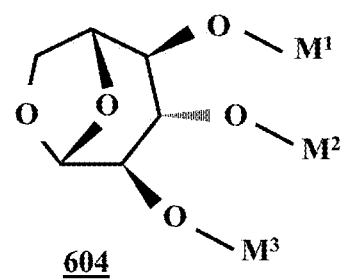
FIG. 6 is a diagrammatic representation of a generic levoglucosan-based flame retardant compound.
Figure 6:
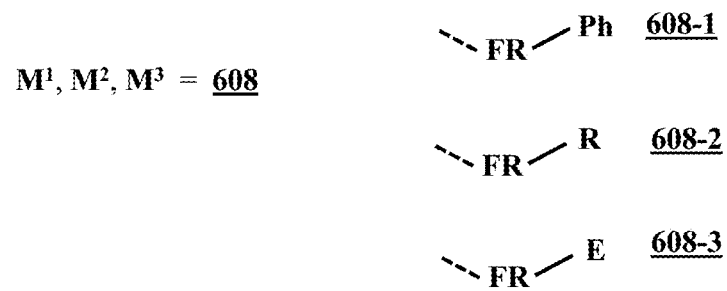

FIG. 6 is a diagrammatic representation 600 of a generic levoglucosan-based flame retardant compound 604. The generic levoglucosan-based flame retardant compound 604 can represent any of the levoglucosan-based flame retardant compounds disclosed herein. The first, second, and third positions on the levoglucosan-based flame retardant compound 604 have $M^1$, $M^2$, and $M^3$ groups, respectively. Each M group can be either a phenyl-FR moiety 608-1, an R-FR moiety 608-2, or an E-FR moiety 608-3. The R groups on the R-FR moieties 608-2 are either $R^1$ (allyl 306 or epoxy 307) or $R^2$ (propylene carbonate 529) groups, and the E groups on the E-FR moieties 608-3 are either phenyl-substituted $E^1$ thioether groups 536, 540, or 544 or functionalized $E^2$ thioether groups 552, 556, or 560. The synthesis and structures of compounds represented by the generic structure 604 are discussed in greater detail with respect to FIGS. 5A-5F.

Figure 7A:
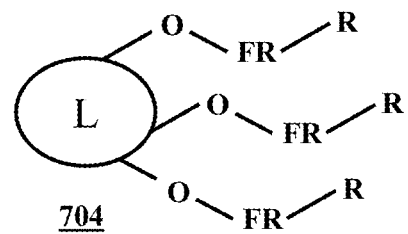
FIG. 7A is a diagrammatic representation of the structures of generic $R^1$ or $R^2$-functionalized levoglucosan-based flame retardant monomers, according to some embodiments of the present disclosure.
Figure 7A:
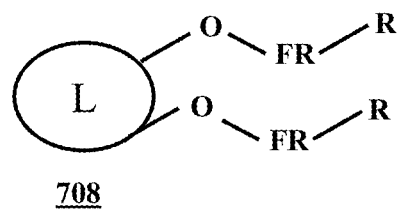
Figure 7A:
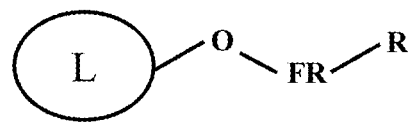

FIG. 7A is a diagrammatic representation of the structures 700 of generic $R^1$- or $R^2$-functionalized levoglucosan-based flame retardant monomers 704, 708, and 712, according to some embodiments of the present disclosure. In FIG. 7A, $R^1$ (allyl 306 or epoxy 307) and $R^2$ (propylene carbonate 529) are referred to as "R" for simplicity. The monomers are R-trifunctionalized levoglucosan-based flame retardant compounds 704 (e.g., compounds 504 and 528), R-difunctionalized levoglucosan-based flame retardant compounds 708 (e.g., compounds 516 and 520), and R-monofunctionalized levoglucosan-based flame retardant compounds 712 (e.g., compounds 512 and 524). The R-functionalized levoglucosan-based compounds 704, 708, and 712 are polymerized to form levoglucosan-based flame retardant polymers. For simplicity, each structure in FIG. 7A shows only ligands with R functional groups (allyl 306, epoxy 307, or propylene carbonate 529). An oval labeled "L" represents the levoglucosan core of each monomer.

Figure 7B:
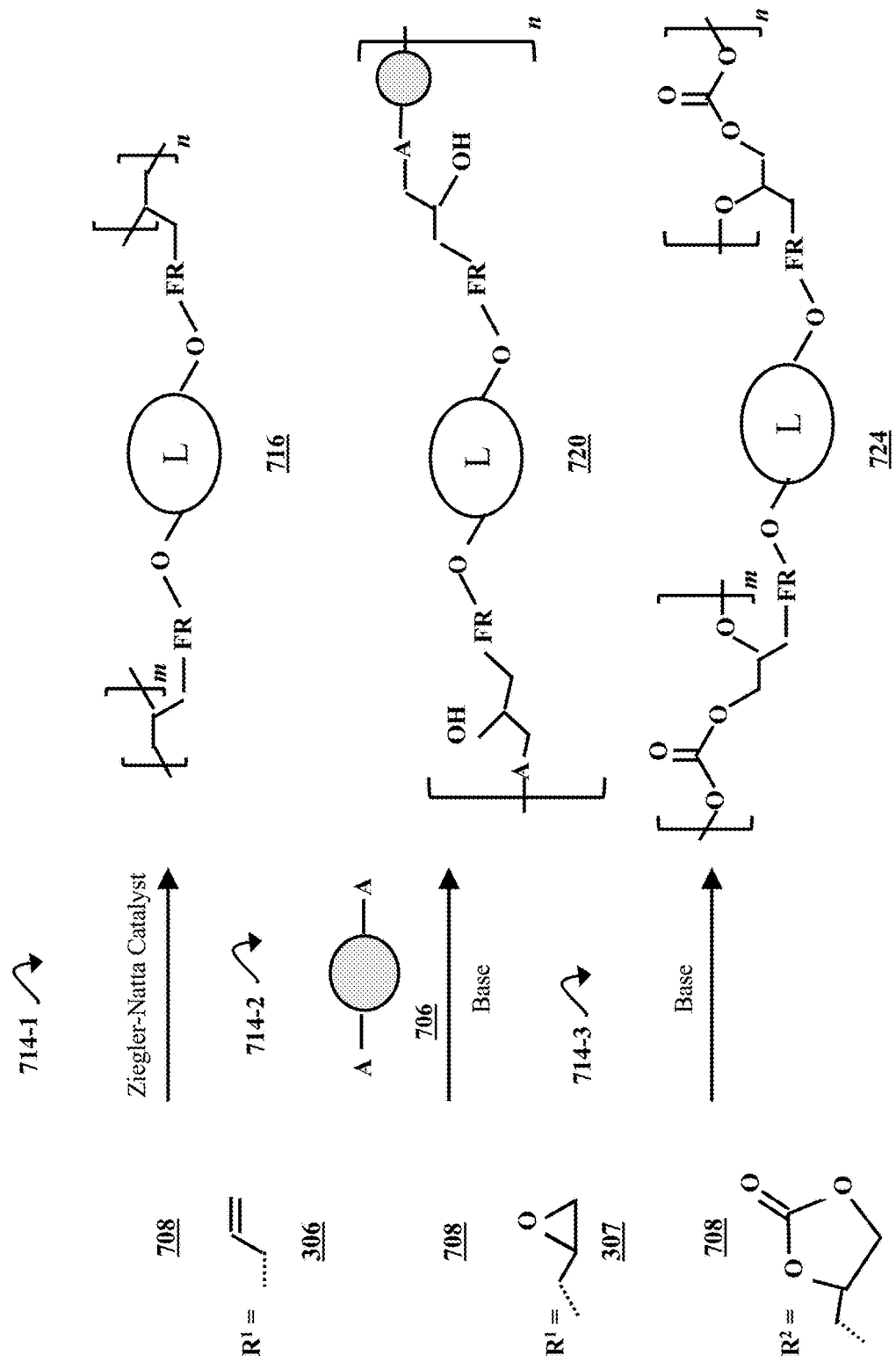
FIG. 7B is a chemical reaction diagram illustrating processes of synthesizing levoglucosan-based flame retardant polymers from levoglucosan-based flame retardant compounds, according to some embodiments of the present disclosure.

FIG. 7B is a chemical reaction diagram illustrating processes 714-1, 714-2, and 714-3 of synthesizing levoglucosan-based flame retardant polymers 716, 720, and 724 from levoglucosan-based flame retardant compounds 708, according to some embodiments of the present disclosure. The reactions illustrated herein are examples of polymers that can be synthesized from the levoglucosan-based flame retardant compounds, but other polymers can be produced as well (e.g., by changing reaction conditions, co-monomers, R groups, etc.).

Processes 714-1-714-3 illustrate the polymerization of R-difunctionalized levoglucosan-based flame retardant monomers 708 only. However, it should be noted that each of these polymerization reactions can also be carried out with the R-trifunctionalized levoglucosan-based flame retardant compounds 704. Additionally, processes 714-1 and 714-3 can be carried out with the R-monofunctionalized levoglucosan-based flame retardant compounds 712. Further, in some embodiments, the polymerization reactions are carried out with a combination of both R-difunctionalized levoglucosan-based flame retardant compounds 708 and R-trifunctionalized levoglucosan-based flame retardant compounds 704, both R-difunctionalized levoglucosan-based flame retardant compounds 708 and R-monofunctionalized levoglucosan-based flame retardant compounds 712, both R-trifunctionalized levoglucosan-based flame retardant compounds 704 and R-monofunctionalized levoglucosan-based flame retardant compounds 712, or a combination of monomers that includes tri-, di-, and monofunctionalized monomers in any ratio.

In process 714-1, allyl-derived levoglucosan-based flame retardant polymers 716 are formed from $R^1$-difunctionalized levoglucosan-based flame retardant compound 708 having allyl $R^1$ groups 306. The $R^1$-difunctionalized levoglucosan-based flame retardant compound 708 is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 714-2, epoxy-derived levoglucosan-based flame retardant polymers 720 are formed from $R^1$-difunctionalized levoglucosan-based flame retardant compound 708 having epoxy $R^1$ groups 307. This $R^1$-difunctionalized levoglucosan-based flame retardant compound 708 is reacted with a base and a second monomer 706. The second monomer 706 is a compound with at least two hydroxyl (—OH) groups or at least two amino (—NH$_2$) groups (e.g., a diol, polyol, diamine, polyamine, etc.) This compound 706 is illustrated as a gray oval with attached A groups. The A groups represent hydroxyl groups or an amino groups. It should be noted that, while two A groups are illustrated herein, there are more than two A groups in some embodiments. Additionally, in some embodiments, the R-difunctionalized levoglucosan-based compound 708 having epoxy $R^1$ groups 307 self-polymerizes under basic conditions. In these instances, the reaction does not include the second monomer 706.

In process 714-3, propylene carbonate-derived levoglucosan-based flame retardant polymers 724 are formed from $R^2$-difunctionalized levoglucosan-based flame retardant compounds 708 having propylene carbonate $R^2$ groups 529. The $R^2$-difunctionalized levoglucosan-based flame retardant monomer 708 is reacted in a ring-opening polymerization initiated by a base. Examples of bases that can be used as initiators can include potassium hydroxide (KOH), sodium hydroxide (NaOH), lithium hydroxide (LiOH), 1,8-diazabicyclo[5.4.0]undec-7-ene (DBU), triazabicyclodecene (TBD), etc.

In addition to the polymers illustrated in FIG. 7B, the levoglucosan-based flame retardant compounds disclosed herein can be used in the synthesis of other flame retardant polymers in some embodiments. An array of classes of flame retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, epoxy resins, polyimides, polyureas, polyamides, poly(vinyl-esters), etc.

One example of an application of polymers that incorporate levoglucosan-based flame retardant compounds is in plastics used in electronics hardware, such as integrated circuit packages. Additional applications can include acoustic dampening, cushioning, plastics, synthetic fibers, insulation, etc. The levoglucosan-based flame retardant compounds can also be used to make adhesives such as bio-adhesives, elastomers, thermoplastics, emulsions, thermosets, etc. Further, materials containing the levoglucosan-based flame retardant compounds can be incorporated into various devices with electronic components that can include printed circuit boards (PCBs), semiconductors, transistors, optoelectronics, capacitors, resistors, chip carriers, etc.

Resins for printed circuit boards (PCBs) can be made flame retardant by incorporating polymers that include levoglucosan-based flame retardant compounds. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the levoglucosan-based flame retardant compounds can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of levoglucosan-based flame retardant compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A levoglucosan-based flame retardant compound with a formula of:

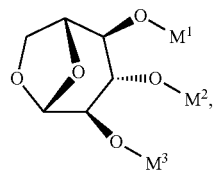

wherein $M^1$, $M^2$, and $M^3$ are phosphorus-based flame retardant groups, and wherein each of the phosphorus-based flame retardant groups has a moiety independently selected from the group consisting of a phosphoryl moiety having the formula:

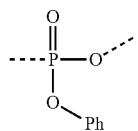

and a phosphonyl moiety having the formula:

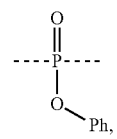

wherein Ph is phenyl.

2. The levoglucosan-based flame retardant compound of claim 1, wherein at least one of the phosphorus-based flame retardant groups is a functionalized flame retardant group.

3. The levoglucosan-based flame retardant compound of claim 2, wherein the functionalized flame retardant group has a functional group selected from a group consisting of an allyl group, an epoxy group, and a propylene carbonate group.

4. The levoglucosan-based flame retardant compound of claim 2, wherein the functionalized flame retardant group has a functional group selected from a group consisting of an amino group, a carboxylic acid group, and a hydroxyl group.

5. The levoglucosan-based flame retardant compound of claim 1, wherein the functionalized flame retardant group has a functional group selected from a group consisting of a carboxylic acid group, a hydroxyl group, and an amine group.

6. A process of forming a levoglucosan-based flame retardant polymer, comprising:
providing levoglucosan;
providing a phosphorus-based flame retardant molecule;
chemically reacting the levoglucosan with the phosphorus-based flame retardant molecule to form a levoglucosan-based flame retardant compound, the levoglucosan-based flame retardant compound including at least one moiety independently selected from the group consisting of a phosphoryl moiety having the formula:

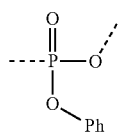

and a phosphonyl moiety having the formula:

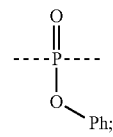

and
incorporating the levoglucosan-based flame retardant compound into a polymer to form the levoglucosan-based flame retardant polymer, wherein Ph is phenyl.

7. The process of claim 6, wherein the levoglucosan is obtained from a bio-based source.

8. The process of claim 6, wherein the levoglucosan-based flame retardant compound is incorporated into the polymer by blending.

9. The process of claim 6, wherein the levoglucosan-based flame retardant compound is incorporated into the polymer by binding the levoglucosan-based flame retardant compound to one or more polymer chains.

10. The process of claim 6, wherein the levoglucosan-based flame retardant compound is incorporated into the polymer by a polymerization reaction.

11. The process of claim 10, wherein the polymerization reaction includes at least one additional monomer.

12. The process of claim 6, wherein the levoglucosan-based flame retardant compound has at least one functional group selected from a group consisting of an allyl group, an epoxy group, a propylene carbonate group, a carboxylic acid group, an amine group, and a hydroxyl group.

13. The process of claim 6, wherein one or more protecting groups are bound to the levoglucosan.

14. An article of manufacture, comprising a material containing a polymer into which a levoglucosan-based flame retardant compound has been incorporated, the levoglucosan-based flame retardant compound having the formula:

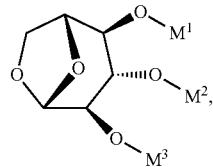

wherein $M^1$, $M^2$, and $M^3$ are phosphorus-based flame retardant groups, and wherein each of the phosphorus-based flame retardant groups has a moiety independently selected from the group consisting of a phosphoryl moiety having the formula:

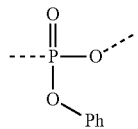

and a phosphonyl moiety having the formula:

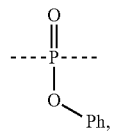

wherein Ph is phenyl.

15. The article of manufacture of claim 14, further comprising an electronic component.

16. The article of manufacture of claim 14, wherein the material is a plastic for integrated circuit packaging.

17. The article of manufacture of claim 14, wherein the material is an adhesive.

* * * * *